United States Patent [19]
Rogers

[11] Patent Number: 4,551,146
[45] Date of Patent: * Nov. 5, 1985

[54] CONNECTOR FOR AMBULATORY DIALYSIS SYSTEM

[75] Inventor: Phillip P. Rogers, Rolling Hills Estates, Calif.

[73] Assignees: Phillip P. Rogers & Faye Rogers Living Trust, Rolling Hills Estates, Calif.; Uatar DTD., Rolling Hills Estates, Calif. ; Phillip P. Rogers & Faye Rogers, co-trustees

[*] Notice: The portion of the term of this patent subsequent to Oct. 19, 1999 has been disclaimed.

[21] Appl. No.: 431,333

[22] Filed: Sep. 30, 1982

Related U.S. Application Data

[63] Continuation-in-part of Ser. No. 157,268, Jun. 9, 1980, Pat. No. 4,354,490.

[51] Int. Cl.⁴ .................................. A61J 7/00
[52] U.S. Cl. .................... 604/403; 604/256; 604/905; 604/283
[58] Field of Search ...................... 128/912; 604/4, 56, 604/7, 256, 265, 280, 283, 403, 905, 29; 285/12, 30, 332, 332.2

[56] References Cited

U.S. PATENT DOCUMENTS

| | | | |
|---|---|---|---|
| 3,307,552 | 3/1967 | Strawn | 604/256 |
| 3,741,217 | 6/1973 | Ciarico | 604/256 |
| 4,334,551 | 6/1982 | Pfister | 604/905 |
| 4,346,703 | 8/1982 | Dennehey et al. | 604/905 |
| 4,354,490 | 10/1982 | Rogers | 604/905 |

FOREIGN PATENT DOCUMENTS 2853635  6/1980  Fed. Rep. of Germany ...... 604/905

*Primary Examiner*—Richard J. Apley
*Assistant Examiner*—Gregory Beaucage
*Attorney, Agent, or Firm*—David O'Reilly

[57] ABSTRACT

A connector for an ambulatory dialysis system which effectively prevents peritoneal infections such as peritonitis. The connector is comprised of a cylinder containing a disinfecting solution which continuously bathes the male and female connectors of a tube during use. A highly absorbent material is packed in the cylinder and saturated with a disinfectant and bathes the male and female connectors when connection is made and continually bathes them during use. A connection is provided by a male fitting on the end of a tube connected to a bag of dialysate fluid or an abdominal opposing tube. Male connector is inserted into the female connector through the cylinder containing the absorbent material saturated with the disinfectant. The absorbent material is packed such that the male connector contacts the absorbent material during insertion to disinfect the opposing ends simultaneously while connection is being made.

14 Claims, 8 Drawing Figures

CONNECTOR FOR AMBULATORY DIALYSIS SYSTEM

This application is a continuation in part of application Ser. No. 157,268, filed June 9, 1980 now U.S. Pat. No. 4,354,490 issued Oct. 19, 1982.

BACKGROUND OF THE INVENTION

This invention relates to connectors for use with ambulatory dialysis devices and more particularly relates to an apparatus which disinfects the connection during connection and use.

There is a new system available for treating patients with loss of kidney function in which a bag of dialysate fluid is connected to the abdominal cavity for the purpose of peritoneal dialysis. In this system, the bag with the dialysate fluid is connected to a permanent abdominal tube and the dialysate fluid is allowed to flow into the peritoneal cavity. The bag and the tubing are then wound around the waist and tied. The dialysate fluid is allowed to remain in the peritoneal cavity for a period of time allowing toxic waste and water to pass into the fluid. At the end of a predetermined period of time, the bag is lowered and the fluid is allowed to flow out and back into the original bag. The bag is then disconnected and discarded and a new bag of dialysate fluid attached to the permanent abdominal tube and the process is repeated.

A frequent problem which occurs from this method of peritoneal dialysis is the danger of peritoneal infection or peritonitis which is extremely high, due to the disconnecting and reattaching of bags with the dialysate fluid. These infections have been occurring even when extreme caution has been taken in making these connections and disconnections. The present method of making the interchange is to thoroughly cleanse the ends of the tubes connected respectively to the bag of dialysate fluid and the abdominal connector before the connection is made. Further, as another precaution, the connection is made with surgically sterile rubber gloves to prevent or guard against any possible peritoneal invasion of bacteria.

Even with these precautions, incidents of peritoneal infection or peritonitis are still high. It would be advantageous if the disconnection and reconnection could be made without going through the time-consuming and very great inconveniencing process of putting on surgically sterile gloves, cleaning both tubes, and then connecting a new bag of dialysate fluid.

SUMMARY OF THE INVENTION

The purpose of the present invention is to permit patients who are on ambulatory peritoneal dialysis systems to make connections and disconnections with a minimum of danger of peritoneal infection.

The present invention was conceived to allow disconnecting and reconnecting a new bag of peritoneal dialysis fluid which minimizes the possibility of any invasion of bacteria into the peritoneal cavity. In the present invention, the male and female connections to the tubes connected to the bag of dialysate fluid and the abdominal connector respectively are surrounded with a disinfectant during the connection and while the dialysate fluid is in use. To accomplish this a cylinder is packed with an absorbent material which is saturated with a disinfectant fluid. As the male and female ends of the respective tubes are brought into engagement they pass through the saturated absorbent material and are connected. The absorbent material contained in the cylinder remains around the connection during the entire use of the dialysate fluid. When a new bag of dialysate fluid is to be attached, the same procedure is repeated, in that the respective ends of the tube are again bathed in disinfectant during and after connection and continuously while in use.

One embodiment further minimizes the danger of contamination of the ends of the tubes being connected. In this embodiment the cylinder is formed as two open-ended, telescoping cylinders which close around the connection of the male and female ends of the tubes and lock them together. An additional advantage of this device is that the open-ended cylinders are attached to and surround the respective male and female end connections of the tubes, acting as shields to minimize any danger of contaminating contact with the ends before, during or after a connection.

It is one object of the present invention to provide a connector for patients using continuous ambulatory peritoneal dialysis.

Another object of the present invention is to provide a method and apparatus for continuously bathing a connector between a bag of dialysate fluid and a tube to an abdominal cavity with a disinfecting solution.

Still another object of the present invention is to provide a method and apparatus for making a connection for continuous ambulatory peritoneal dialysis which is simple and easy to use.

Yet another object of the present invention is to provide a method of connecting a bag of dialysate fluid for continuous ambulatory peritoneal dialysis which provides shields for the end of the tubes being connected to prevent contamination.

These and other objects of the invention will become apparent from the following detailed description when considered in conjunction with the drawings, wherein like reference numbers identify like parts throughout.

DETAILED DESCRIPTION OF THE PREFERRED EMBODIMENT

Figure 1:
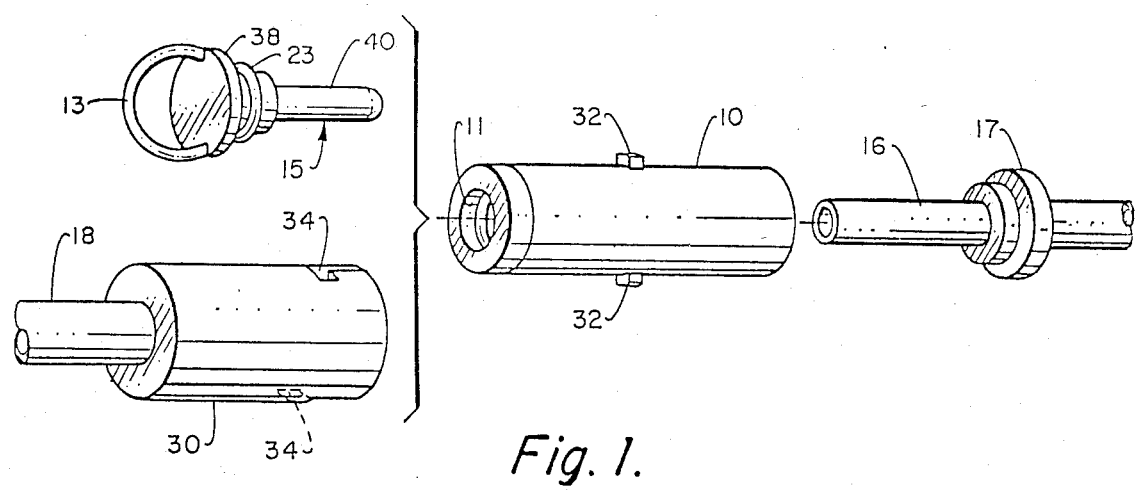
FIG. 1 is an exploded view of the first embodiment of the peritoneal dialysis connector of the present invention.

Referring to FIG. 1, the peritoneal dialysis connector is comprised of a cylinder 10 which attaches to a collar 17 on a first tube 16. A second open-ended cylinder 11 is attached to the end of a separate tube 18 for telescopic engagement with the first cylinder 10 which will be described in greater detail hereinafter. Also provided with the device is a plug 15 for sealing the end of cylinder 10, as will be described hereinafter.

Figure 2:
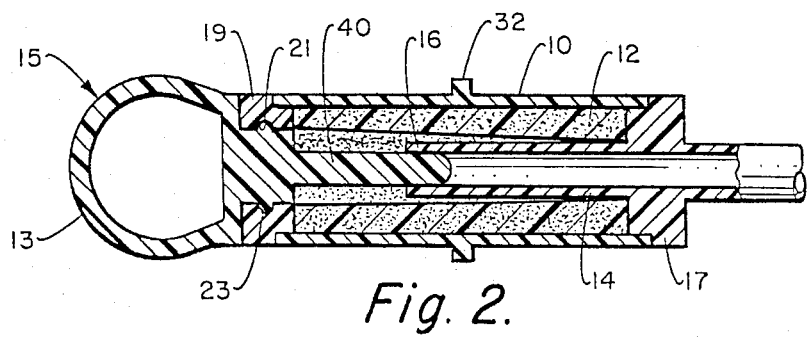
FIG. 2 is a sectional view of one end of the peritoneal dialysis connector.

The cylinder 10 on the end of tube 16 is illustrated in greater detail in FIG. 2. Inside the cylinder 10 a packing of absorbent material 12, such as a sponge, is provided. This sponge is saturated with a disinfectant solution, such as Betadine. Cylinder 10 is attached to collar 17 by a suitable adhesive. With the cylinder 10 connected to the collar 17, the disinfectant solution in the absorbent material 12 cleanses the end of tube 16. A cap ring 19 closes the opposite end of the cylinder 10. Cap ring 19 is provided with a groove 1 for engagement by a ridge 23 on plug 15. The end of cylinder 10 is sealed by the plug 15 by inserting the plug until the shank 40 engages the end of tube 16 and the ridge 23 locks into place in groove 21 with cover 38 closing and sealing the opening in cap ring 19. This seals the cylinder until it is ready to use preventing bacterial contamination and evaporation of the disinfectant solution.

Figure 3:
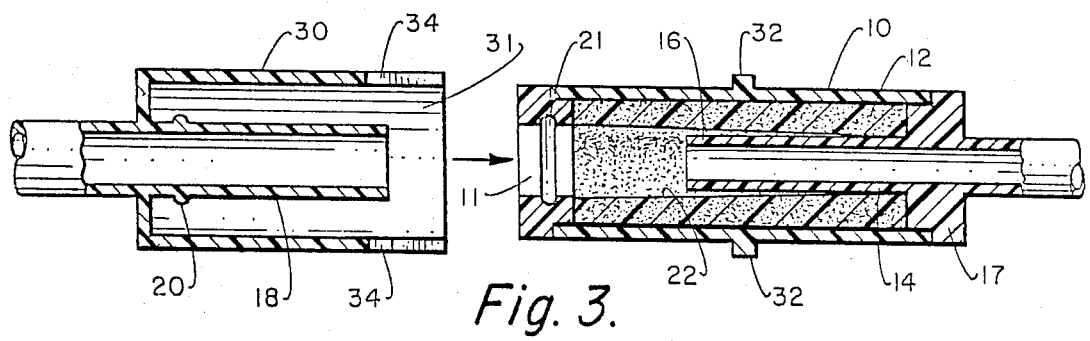
FIG. 3 is a partial sectional view of the end of the peritoneal dialysis connector prior to connection.

The other tube 18 has a cylinder or sleeve 30 attached to it as shown in FIG. 3. The cylinder 30 extends beyond the end of the tube 18, preventing contact with fingers or any potential contaminating means. The end of the tube 18 is provided with a ridge 20 similar to the ridge 23 on the plug 15. The open end 31 of cylinder 30 may be closed in some fashion by a wrapping or some other suitable means prior to use to minimize the possibility of contamination during shipment.

Figure 4:
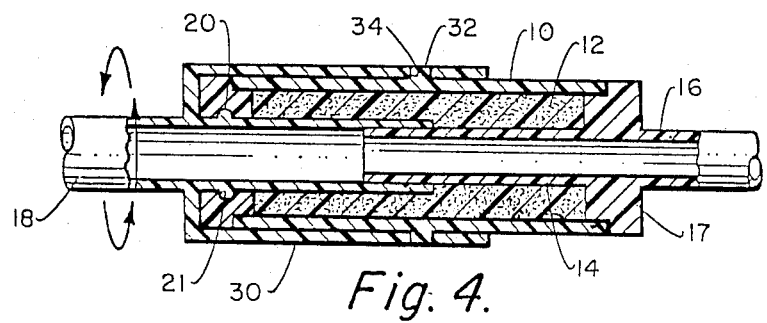
FIG. 4 is a sectional view illustrating the connection of the peritoneal dialysis connector of the present invention.

To use the device the plug 15 is removed from the cap ring 19 by pulling on the ring 13. This opens the cylinder 10 for insertion of the end of the tube 18. The tube 18 passes through the opening 11 in the cylinder 10 and engages the end tube 16. Simultaneously the cylinder 30 telescopically engages the cylinder 10. The passageway 22 in the absorbent material 12 is intentionally slightly smaller than the outside diameter of tube 18, causing the tube to engage the absorbent material and be bathed in disinfectant solution as the connection is being made. When the tube 18 is fully inserted in the cylinder 10, the rib 20 will engage the groove 21 as illustrated in FIG. 4.

To lock the connection, a pair of L-shaped slots 34 are provided in the cylinder 30 which engage lugs 32 on the cylinder 10. The lugs 32 slide into the slots 34 and by a slight twisting motion are locked in the leg of the L-shaped slot 34. Thus the tube 18 is connected to the tube 16 and is completely sealed and surrounded by the connection of the telescoping cylinders 10 and 30. Also, the disinfecting solution 12 has bathed the ends of the tubes 16 and 18 during connection and continues to bathe the ends during use.

As can be seen, the connection can be made by grasping the tubes 16 and 18 behind the ends of the telescoping cylinders 10 and 30 and no contact with the ends of the tubes need be made. Further, the connection is cleansed, disinfected and simultaneously connected in the minimum amount of time substantially eliminating the possibility of contamination.

Figure 5:
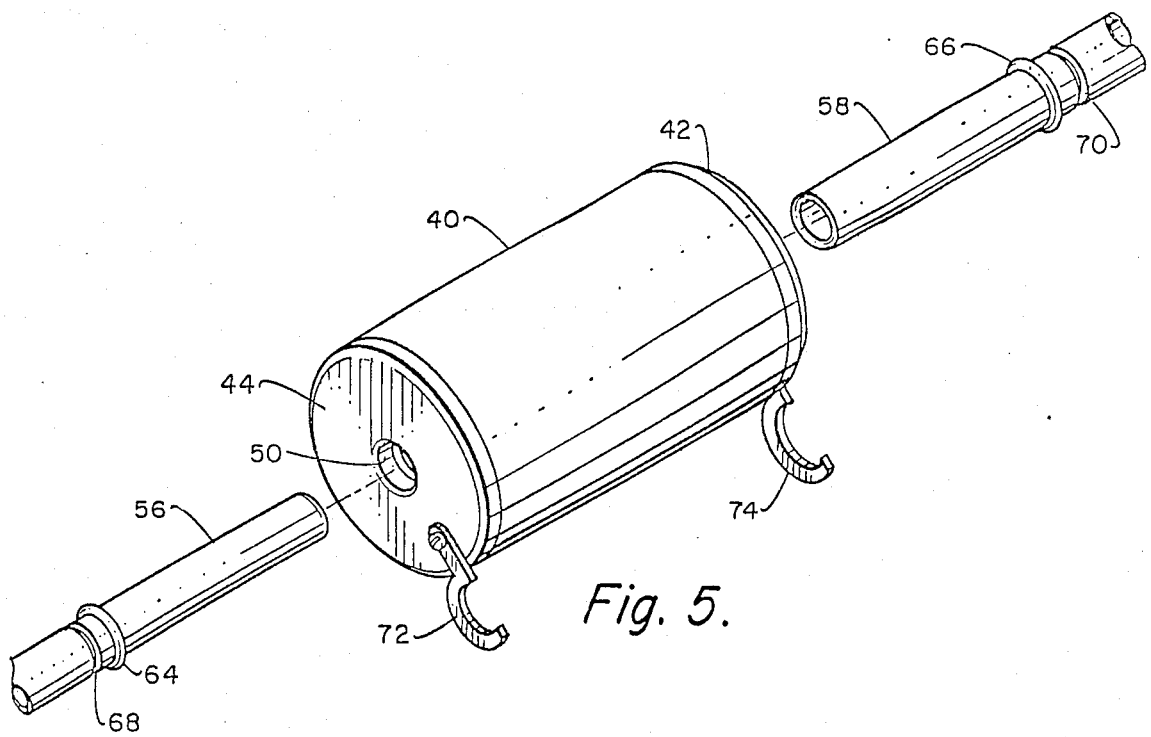
FIG. 5 is an alternate embodiment of the peritoneal dialysis connector.
Figure 6:
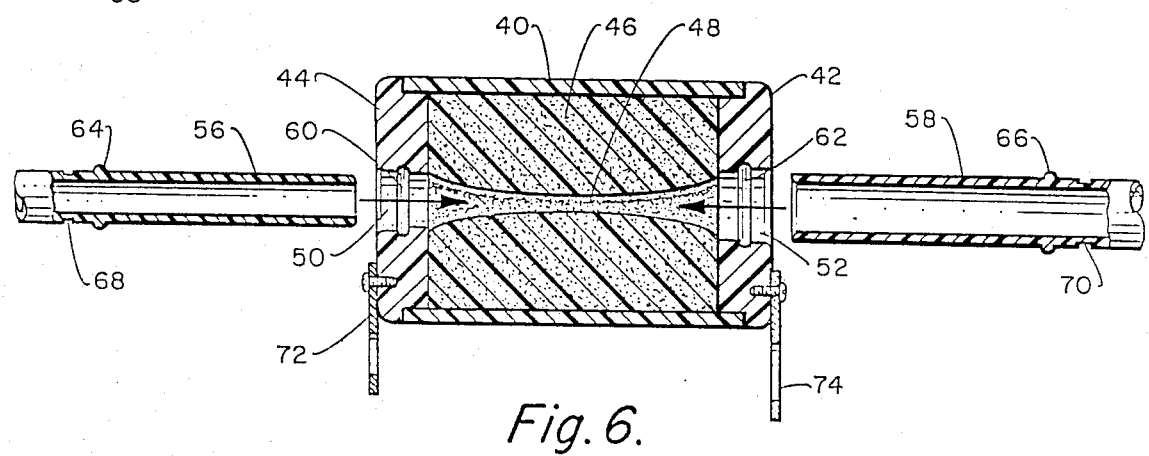
FIG. 6 is a sectional view illustrating the peritoneal dialysis connector of FIG. 5.
Figure 7:
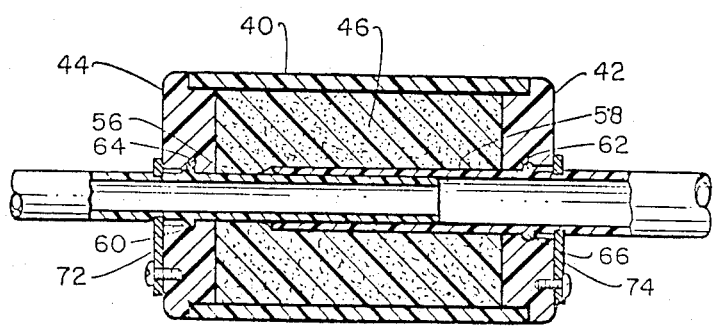
FIG. 7 is a sectional view of the peritoneal dialysis connector of FIG. 5 illustrating the device being connected.

An alternate construction is illustrated in FIGS. 5 through 7. In this embodiment the cylinder 40 is separate from the connectors and has end connectors 42 and 44 sealed to the cylinder 40 by suitable adhesive. The interior of the cylinder 40 has an absorbent material 46 suitably saturated with a disinfecting solution as before. In this embodiment, however, the pasageway 48 between the open ends and end 52 is tapered toward the center and is generally smaller in diameter than the tubes 56 and 58. Grooves 60 and 62 are provided which mate with ribs 64 and 66 on the respective tubes; to seal the openings 50 and 52 when the tubes are in engagement. The tubes 56 and 58 are also provided with grooves 68 and 70 for locking the connection by means of pivoting hooks 72 and 74, as will be described hereinafter.

To make this connection, the male tube 56 would be inserted through opening 50 in the cylinder 40 until the ridge 64 locks in the groove 60 and the tube is secured by hook 72. The other tube 58 would then be inserted through the hole 52 in cylinder 40 until it engages the end of tube 56, as shown in FIG. 7. Preferably, the tube having the male connector is inserted first. The outside of the tube will be completely bathed in disinfecting solution, thus carrying some disinfecting solution into the interior of the female connector, in this case tube 58. Tube 58 is inserted until the ridge 66 locks into groove 62 and the hook 74 is then fitted into engagement with the slot 70 locking the device together. Thus, the connection of tubes 56 and 58 is made through a disinfecting solution which continues to bathe the connection during the use of the dialysate fluid.

A disadvantage of the second embodiment is that the ends of the tubes 56 and 58 may be exposed for a brief period. Since the danger of bacterial infection is great, it is preferable to shield the ends of the tubes, as shown in the embodiment of FIG. 1 or minimize their exposure to as brief a period as possible. In the latter embodiment, however, the cylinder 40 is not fixed to the tube 56 and can be replaced as desired. Alternately, the cylinder 10 on the embodiment of FIGS. 1 through 4 could be made removable in the manner illustrated with the embodiments of FIGS. 5 through 7. Also preferably the cylinder 10 with the absorbent packing would be provided on the tube connected to the bag of dialysate fluid for replacement each time a connection is made. Thus, a fresh supply of disinfecting solution in the absorbent material 12 will be provided with each connection.

Figure 8:
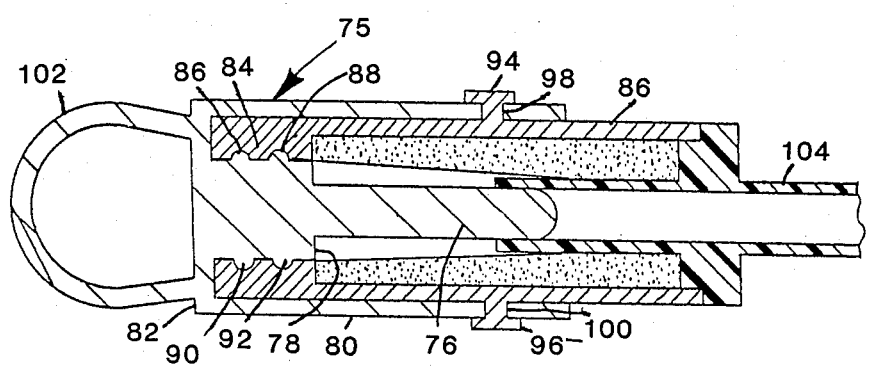
FIG. 8 is a sectional view showing an alternate embodiment of the peritoneal dialysis connector illustrated in FIG. 2.

An alternate method of sealing the cylinder 10 on the end of tube 16 is shown in FIG. 8. This method combines a second cylinder with a plug similar to plug 15 of FIG. 2. A plug 75 is provided with a shank 76, a shoulder 78 and a cylinder 80 attached to cover plate 82. The cap ring 84 is formed integrally with cylinder 86 and has a pair of grooves or recesses 86 and 88. The shoulder 78 on the plug has a pair of ridges 90 and 92 engaging the recesses 86 and 88 respectively.

In addition to the retention of ridges 90 and 92 in recesses 86 and 88 a positive locking mechanism may be provided in the form of posts 94 and 96 engaging and locking into slots 98 and 100 of cylinder 80. This would be a twist locking action applied to ring 102 similar to that illustrated in FIG. 4. When plug 75 is fully pushed in and locked, ridges 90 and 92 will seat in recesses 86 and 88 and shank 76 will engage the end of tube 104.

Obviously, many modifications and variations of the present invention are possible in light of the above teachings. It is to be understood that the scope of the invention is to be limited only by interpretation of the appended claims.

What is claimed is:

1. A peritoneal dialysis fluid connecting device comprising;
    enclosure means;
    an absorbent packing material in said enclosure means;

said absorbent packing material being substantially saturated with a disinfectant solution;

a first tube connecting end for supplying a peritoneal dialysis fluid;

a second tube connecting end adapted to telescopically mate with and connect to said first tube connecting end;

means allowing said first and second tube connecting ends to be telescopically mated inside said enclosure means so that the connecting ends are bathed in said disinfectant solution when the connection is being made and throughout use.

2. The device according to claim 1 in which said retaining means comprises; a ring attached to the open end of said cylinder; a recess in said ring; a shoulder on the shank of said plug; a ridge on said shoulder adapted to engage and lock into the recess in said ring.

3. The device according to claim 2 in which said sealing means for sealing said cylinder comprises:

a second open-ended cylinder on said plug having an internal diameter approximately equal to the outside diameter of the first open-ended cylinder; said second open-ended cylinder adapted to slide over and seal the first cylinder when said plug shank engages said connecting tube end.

4. The connecting device according to claim 1 in which said means for allowing said first and second tube connecting ends to be telescopically mated inside said enclosure means comprises a passageway passing through said enclosure means.

5. The connecting device according to claim 4 in which said enclosure means is separate from said first and second tube connecting ends.

6. The connecting device according to claim 5 in which said enclosure means is a hollow cylindrical means having openings at each end in communication with a passageway through said absorbent packing material for receiving said first and second connecting ends.

7. The connecting device according to claim 4 in which said enclosure means is formed around and attached to one of said connecting ends.

8. The connecting device according to claim 7 in which said enclosure means is a hollow cylindrical means having openings at each end in communication with a passageway through said absorbent packing material for receiving said first and second connecting ends.

9. The connecting device according to claim 6 in which said enclosure means comprises a pair of enclosures formed on the ends of each of said first and second tube connecting means constructed to mate when said first and second tube connecting ends mate.

10. The connecting device according to claim 9 in which said pair of enclosures extend beyond the respective ends of said first and second tube connecting ends to shield said tube connecting ends from contamination whereby said pair of enclosures mate before said tube connecting ends mate.

11. The connecting device according to claim 6 in which said passageway is formed in said absorbent packing material to be smaller than the diameter of said first and second tube connecting ends so that said first and second tube connecting ends make contact with and displace said absorbent material and are bathed in said disinfectant solution when said connection is being made.

12. The connecting device according to claim 11 including sealing means for sealing said openings to said passageway to exclude contaminants.

13. The connecting device according to claim 12 in which said sealing means includes removal means constructed and arranged to allow removal without contaminating the interior of said enclosure means.

14. The connecting device according to claim 13 in which said sealing means comprises a disposable plug means inserted in said passageway; said plug means including means covering and sealing the open ends of said enclosure means; and retaining said plug in said enclosure means.

* * * * *